United States Patent [19]

Burton et al.

[11] Patent Number: 5,052,395
[45] Date of Patent: Oct. 1, 1991

[54] NON-INVASIVE ULTRASONIC PULSE DOPPLER CARDIAC OUTPUT MONITOR

[75] Inventors: Thomas A. Burton; George F. Sedivy, both of Rochester, N.Y.; John R. Klepper; Mark A. Moehring, both of Seattle, Wash.; Richard F. Ferraro, Lake Forest, Wash.; Donald L. Davis, Seattle, Wash.

[73] Assignee: Waters Instruments, Inc., Rochester, Minn.

[21] Appl. No.: 499,292

[22] PCT Filed: Nov. 16, 1988

[86] PCT No.: PCT/US88/04084
§ 371 Date: May 16, 1990
§ 102(e) Date: May 16, 1990

[87] PCT Pub. No.: WO89/04634
PCT Pub. Date: Jun. 1, 1989

Related U.S. Application Data

[63] Continuation-in-part of Ser. No. 120,882, Nov. 16, 1987, abandoned.

[51] Int. Cl.⁵ .................................................. A61B 8/00
[52] U.S. Cl. .......................... 128/661.09; 128/661.08; 128/661.1
[58] Field of Search ............... 128/660.1, 661.1, 61.08, 128/661.09, 662.01, 661.01

[56] References Cited

U.S. PATENT DOCUMENTS

| | | | |
|---|---|---|---|
| 4,501,277 | 2/1985 | Hongo | 128/661.09 |
| 4,509,526 | 4/1985 | Barnes et al. | 128/661.1 |
| 4,608,993 | 9/1986 | Albert | 128/662.01 |
| 4,790,322 | 12/1988 | Iinuma | 128/661.1 |

Primary Examiner—Francis Jaworski
Assistant Examiner—George Manuel
Attorney, Agent, or Firm—James R. Haller; Gregory P. Kaihoi; Mary P. Bauman

[57] ABSTRACT

A cardiac output measurement device for the real-time, non-invasive measurement of cardiac output that can be effectively operated by relatively unskilled personnel on a routine monitoring basis in a wide variety of office and hospital conditions. To accomplish this task, the system utilizes a pulsed Doppler ultrasound transducer directed through the suprasternal notch of a patient axially towards the blood flow in the ascending aorta. The device automatically searches the ascending aorta at various predetermined depths to find the depth at which the greatest quality blood velocity reading is detected. An examination is performed at that chosen depth and the device automatically calculates a patient's cardiac output from the Doppler measured velocity combined with an aortic diameter estimation made from the patient's height, weight, and age. The device automatically calculates cardiac velocity, cardiac index, stroke distance, heart rate, and stroke volume.

11 Claims, 11 Drawing Sheets

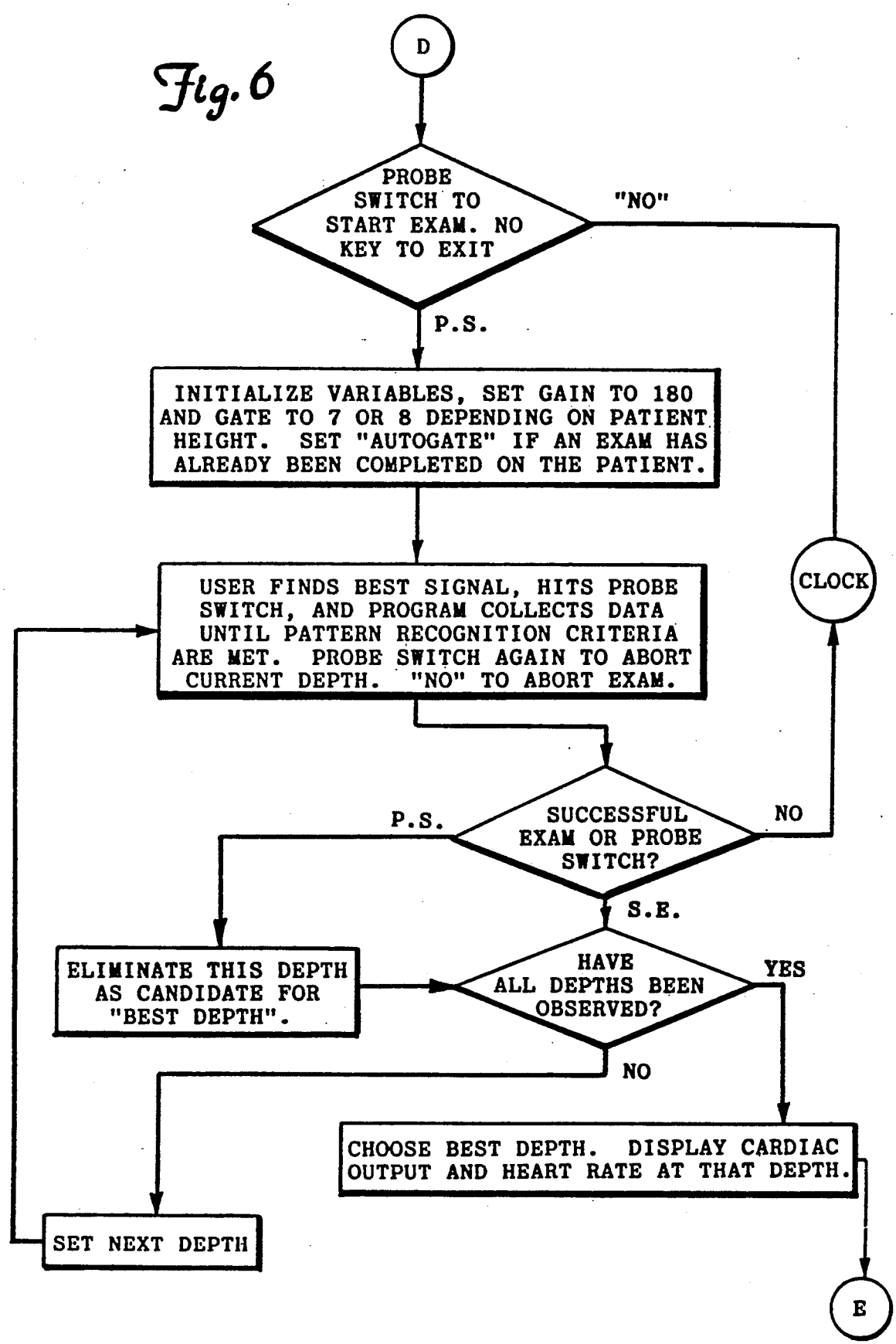

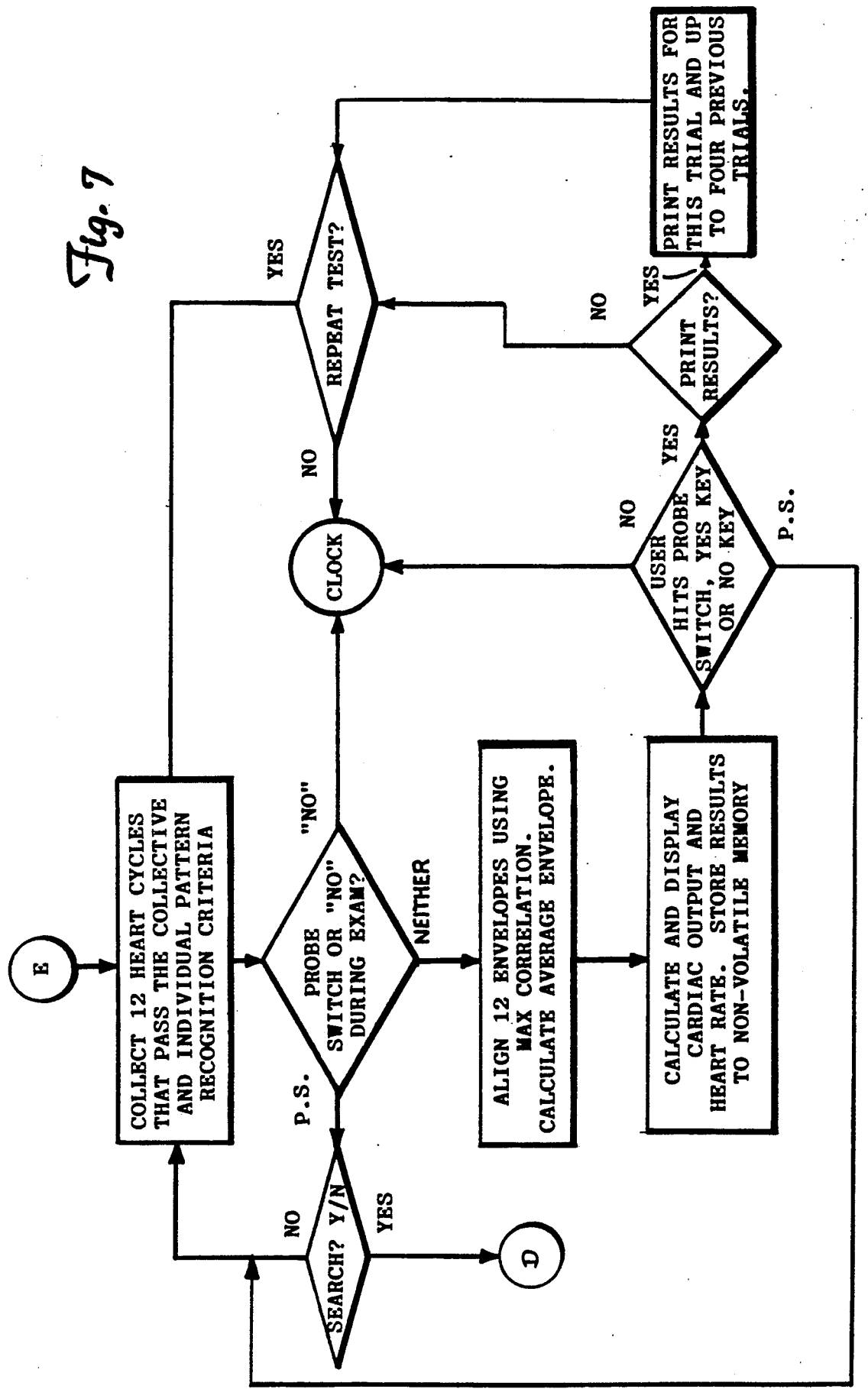

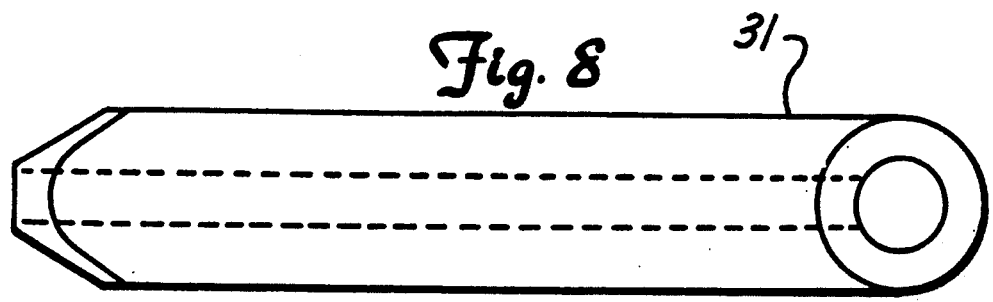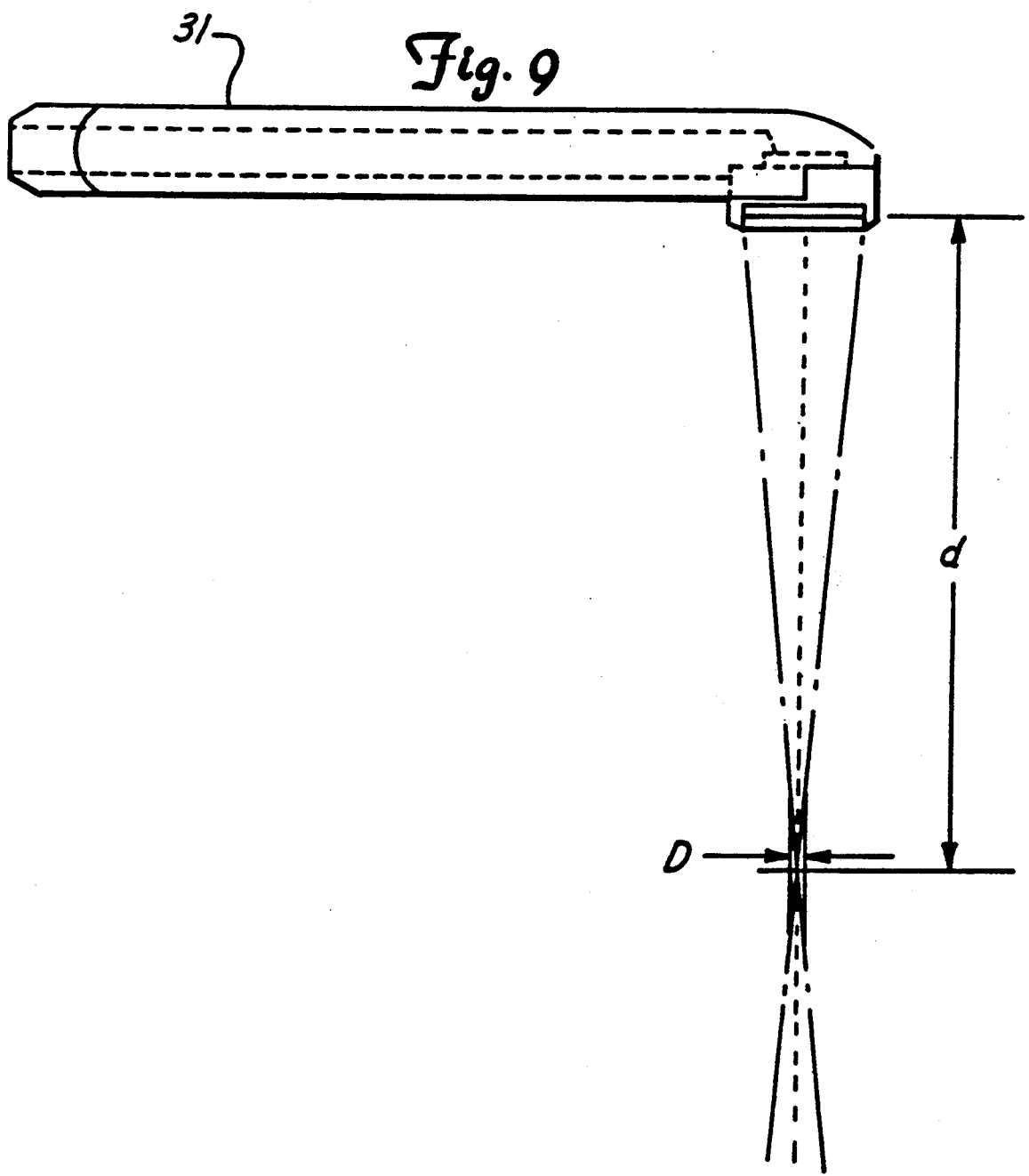

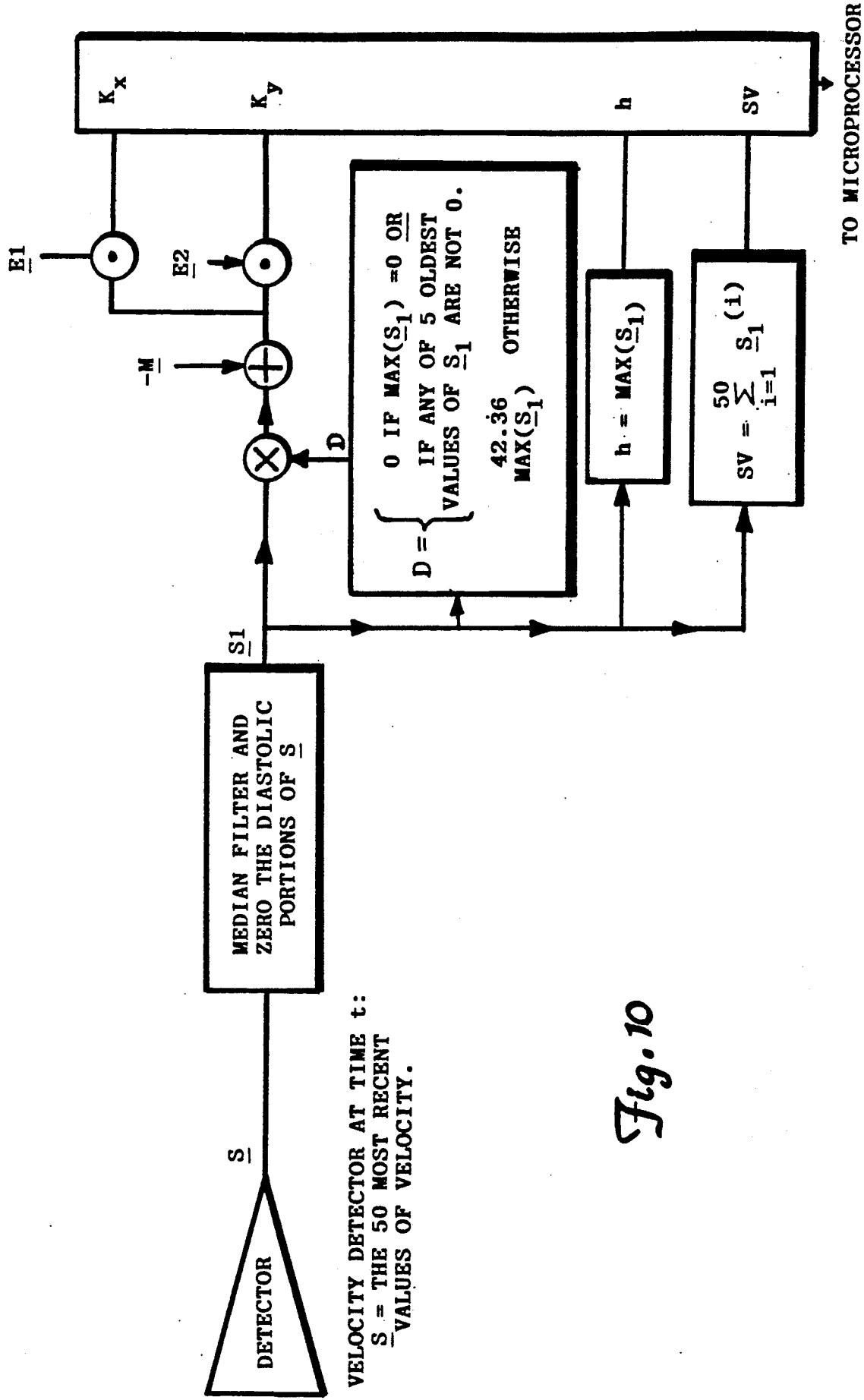

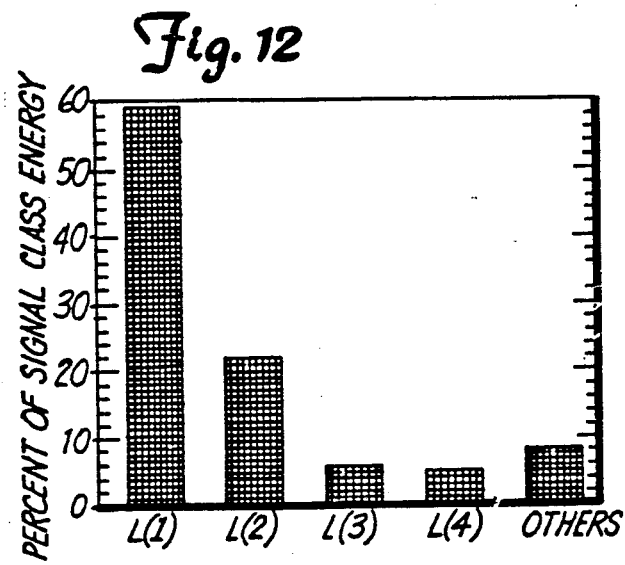
Fig. 12
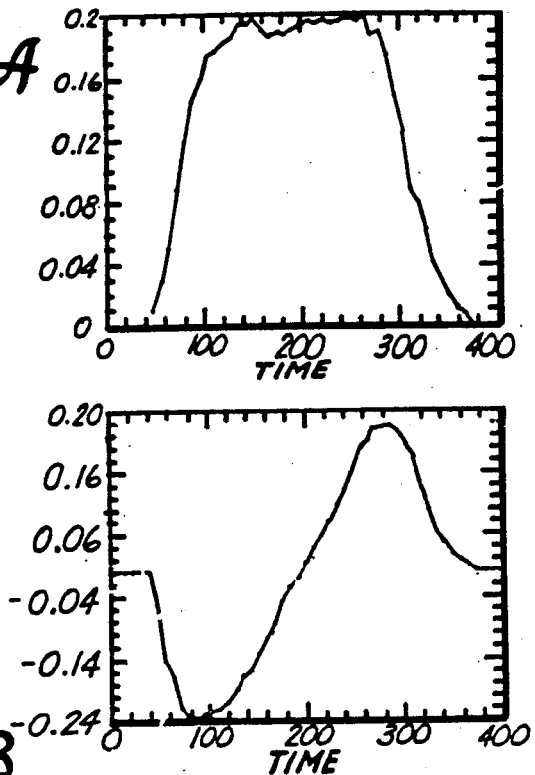
Fig. 13A
Fig. 13B
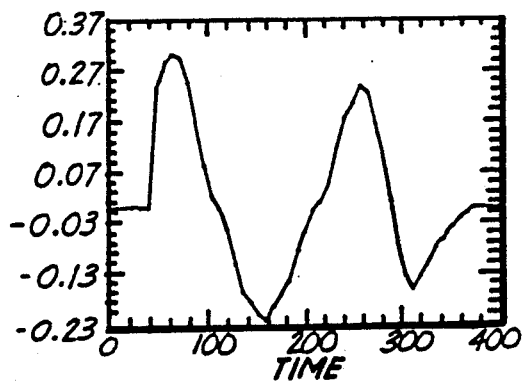
Fig. 13C
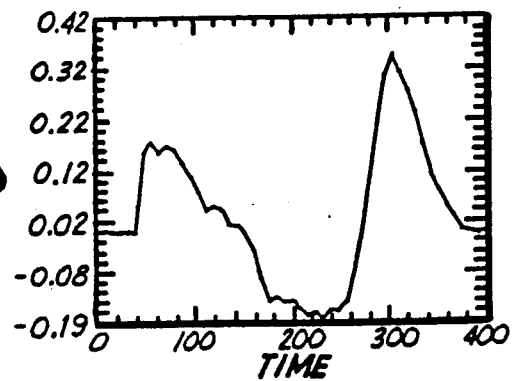
Fig. 13D 5,052,395

NON-INVASIVE ULTRASONIC PULSE DOPPLER CARDIAC OUTPUT MONITOR

RELATED APPLICATIONS

This application is a continuation-in-part of U.S. patent application Ser. No. 120,882 filed on Nov. 16, 1987, now abandoned.

FIELD OF THE INVENTION

The invention relates to a device for the non invasive measurement of cardiac output, and more specifically to a device for the non-invasive measurement of cardiac output of a human by means of a pulse-Doppler insonification technique.

BACKGROUND OF THE INVENTION

It is particularly desirable at times to measure the cardiac output of a patient on a real time basis without employing invasive surgical techniques. Non-invasive measurement of cardiac output using Doppler ultrasound has been a goal for many years. Success has been reported using duplex imaging equipment by combining either echographic or M-mode measurement of aortic diameter as measured from the second or third intervostal space with Doppler velocity measurements performed from the suprasternal notch. Good correlation with thermodilution cardiac output measurements have been reported using these techniques. The primary drawback of these techniques is the requirement for relatively expensive equipment and highly skilled operators to perform the measurement.

Several previous approaches to making a dedicated instrument to compute cardiac output have used continuous wave Doppler from the suprasternal notch of a patient. These techniques relied upon CW Doppler to measure blood flow velocities in the ascending aorta, the aortic arch, or the descending aorta. Although these implementations proved quite successful in the hands of skilled operators, routine clinical application was made more difficult by the potential confusion of signals that may occur with CW Doppler. When measurements are attempted for flow in the ascending aorta, it is not uncommon to also find flow signals in the same area from the innominate artery on the right or the left carotid or subclavial arteries to the left. Although a window is generally available in which only the aortic signal can be found, an unskilled operator may have difficulty determining the difference between these signals from the aorta and other such signals available from the innominate carotid, or subclavian arteries. Flow signals measured from the aortic arch or descending aorta are potentially less representative of total cardiac output due to Doppler angle, as well as the lack of knowledge of the unknown percentage of flow which has been directed to the head. Flow measurements in the descending aorta may provide a good trend indicator but cannot readily provide absolute cardiac output information.

In the past, one method used to measure the cardiac output of a patient required a doctor to anesthetize a patient and insert an ultrasonic transducer probe in the esophagus near the aorta of the heart with much discomfort to the patient. Another method of cardiac output measurement involved the surgical insertion of a detector in the pulmonary artery of a patient. Use of this method was generally limited to extremely ill patients because it is a particularly risky operation.

Since continuous wave (CW) Doppler devices do not provide any range discrimination, no means is available for limiting the range distance from the transducer along the direction of the ultrasonic beam so that the measurement being taken may be optimized to correspond where the best reading for cardiac output velocity should be taken. This "best" location corresponds to a point approximately 2 cm above the annulus of the aortic valve at which point any turbulence associated with a normal aortic valve has diminished and a more or less uniform flow profile exists across the area of the aorta. It is not possible, when using continuous wave insonification, to uniquely determine the location along the ultrasonic beam from which a returning energy wave was reflected, to determine precisely where the reading came from, and if the reading represents blood flow in the ascending aorta. These systems require an ultrasound technician or a cardiologist to accurately analyze the output of the device. U.S. Pat. No. 4,509,526 discloses a device that uses continuous wave insonification to measure the blood flow velocity in the ascending aorta of a patient which is combined with a separate measurement of aortic diameter to provide a measure of cardiac output. This device requires a highly skilled ultrasound technician or a cardiologist to operate and to interpret the tracer display to receive a valid cardiac output velocity reading. The system does not have the ability to detect aortic velocity selectively at different distances from the transducer due to the fact that it uses continuous wave ultrasound. The device also does not have the capability to distinguish between signals representing noise or other reflected signals and signals representing blood flow in the ascending aorta.

SUMMARY OF THE INVENTION

The invention relates to a method and device for the automatic measurement of blood velocity in the ascending aorta utilizing pulse Doppler ultrasound and having the capability of automatically searching for the optimal measurement of blood velocity at different depths in the ascending aorta of a patient. The cardiac output monitor of the invention interacts with the user through a visual display, a printer, and a keyboard. The user may input various parameters and data about the patient through the keyboard. Values corresponding to a patient's height, weight, and age are input into the device, from which a value for the patient's aortic cross sectional diameter is estimated using an established formula. Alternatively, a value for aortic cross-sectional diameter obtained from another method may be input into the device and used to calculate stroke volume, cardiac output, etc.

The device performs multiple signal processing tasks simultaneously in real time. The received RF signals are demodulated to provide Doppler shift signals in the audio frequency range which correspond to blood flow velocities. The Doppler shift signals are analyzed in the frequency domain to determine a modal or average Doppler shift frequency for each instant in time. A visual bargraph of these modal or average frequencies is displayed on the front of the instrument. A time series of the modal or average frequencies hereafter designated AVP (aortic velocity profile) is formed and processed to yield such parameters as heart rate, stroke distance, maximum velocity, and other pertinent statistical parameters including Karhunen-Loeve expansion coefficients used in pattern recognition algorithms.

The device emits a real time audio signal, proportional to blood flow velocity detected in the ascending aorta of a patient. The operator can use this signal, as well as the visual display, to position a transducer, thereby obtaining a Doppler shift signal from the ascending aorta. A sophisticated signal pattern recognition system is employed in the device to analyze the time series of modal or average frequencies and check it against several criteria before it is confirmed to be a time series corresponding to flow within the ascending aorta. If the time series does not pass the criterion, it is rejected and the operator must reposition the transducer probe to find a better signal.

The sampling and pattern recognition are performed continuously to try to obtain signals which are within the established range of pattern recognition criteria. The device will automatically search for blood flow velocity at different depths in the aorta and will compute an average maximum value for blood flow velocity at each of the depths searched. The depth at which the device detects the greatest average peak systolic blood flow velocity is the depth that is chosen by the device to perform the examination. As soon as a sufficient number of signals pass the pattern recognition criteria at this depth, the examination is automatically terminated and the results are presented to the operator on the visual display, or the printer if chosen.

The transducer probe of the device is designed to fit within the suprasternal notch of a patient with minimal discomfort to insonify a region of the ascending aorta to detect blood flow velocity.

BRIEF DESCRIPTION OF THE DRAWINGS

FIG. 6 is a schematic diagram of "Acquisition" mode utilized in the device of the invention; and FIG. 7 is a schematic diagram of "Acquisition Calculation" mode utilized in the device of the invention.

FIG. 8 is a bottom view of the transducer probe utilized in the device of the invention;

FIG. 9 is an elevation view of the transducer probe utilized in the device of the invention;

FIG. 10 is a schematic diagram of a portion of the real time pattern recognition mode utilized in the device of the invention;

FIG. 12 is a bar graph showing relative signal class energy corresponding to the eigenvectors of FIG. 13; and FIG. 13 shows a plurality of graphs showing the eigenvectors corresponding to the eigenvalues of FIG. 12.

DETAILED DESCRIPTION OF THE PREFERRED EMBODIMENTS

General Approach

Figure 1:
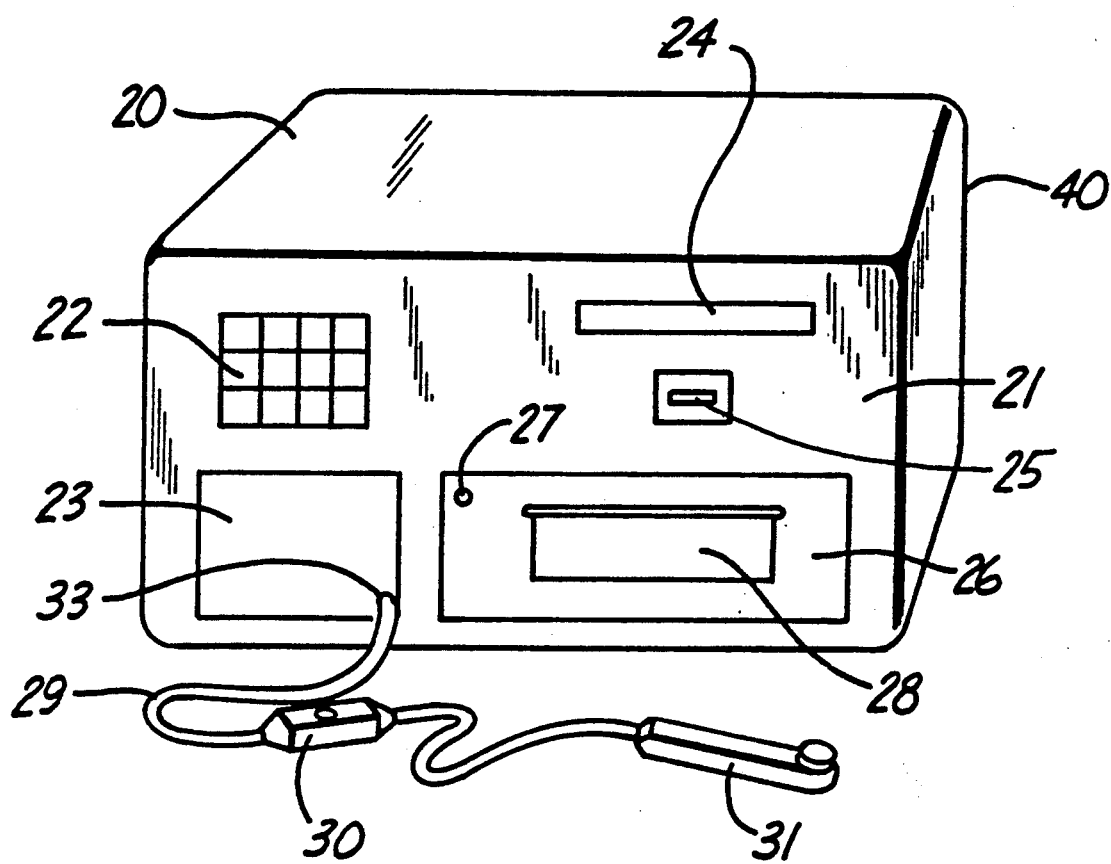
FIG. 1 is a perspective view of the device of the invention.

In general, use of pulse Doppler ultrasound in a "blind" search mode is considered more difficult without the aid of an accompanying image. The device of the invention operates in a "blind" search mode. To get around this difficulty, the system has a series of range gates provided at depths certain to be beyond the innominate artery in order to measure flow in the ascending aorta. An initial depth of range gate is selected by the instrument based upon the subect's height. This initial search depth is used to locate the flow in the ascending aorta.

The device provides the operator with information about blood velocity in the ascending aorta so that the optimal location for measurement of blood velocity may be found. The user manipulates the transducer in the suprasternal notch of the patient and the Doppler range gate is automatically stepped through a search from 7 to 10 cm. During this "search in depth", the device performs real time pattern recognition of the received signals, and saves those signals which pass the pattern recognition criteria. Once the optimum depth is determined, the cardiac output and heart rate, as determined at that depth, are displayed. The device then returns to that depth and acquires data for a repeat measurement of cardiac output. Typically, the entire examination takes 1 to 2 minutes to perform and may be easily repeated with minimal discomfort to the patient.

Several assumptions underlie the method the device uses for computing blood velocity. These assumptions are common to all of the Doppler measurement techniques described above.

The first assumption is that the angle between the Doppler beam and the direction of flow in the ascending aorta is zero degrees. The velocity of blood flow detected by Doppler ultrasound techniques is directly proportional to the Doppler shift frequency. In computing blood flow velocity using Doppler ultrasound, the only angular dependence is a cosine factor of the angle between the Doppler beam and the direction of blood flow being measured. The cosine factor is not considered a significant limitation or source of error because a moderate angle produces a very small error in the velocity calculation.

The second major assumption is that systolic flow in the ascending aorta can be characterized as plug flow. Plug flow assumes a blunt flow profile across the aortic flow diameter. The assumption of plug flow during systole in the ascending aorta appears well justified with some exceptions. The flow stream diameter is generally stated to be equivalent to the diameter of the aortic valve which is typically equal to the aortic diameter just above the sinus under normal circumstances. One exception occurs when patients have aortic stenosis. In this instance, the flow diameter may be significantly less than the flow diameter of the ascending aorta. Therefore, use of this instrument on patients with aortic stenosis is not valid unless the orifice diameter is known. Another condition which would compromise the cardiac output result of this device would be aortic insufficiency in which case the regurgitant flow fraction of blood would be unknown. In addition, any other condition which might produce extreme turbulence in the ascending aorta could compromise the results.

In order to compute volume flow of blood, the cross sectional area of the ascending aorta, the heart rate, and the flow velocity integral, or stroke distance, must be determined. The stroke distance is defined as the area under the mean velocity profile per beat. The stroke distance multiplied by the cross-sectional area produces the stroke volume and the stroke volume multiplied by heart rate produces the cardiac output measurement.

A key factor in making a reliable and easy-to-use instrument is to provide a device capable of making almost instantaneous automated calculations to steer the user to the correct signals as well as notifying the user of signal characteristics indicative of patient conditions which would make the measurement unreliable. Pattern recognition techniques are employed to analyze the time series modal frequency waveforms in order to determine the efficacy of any individual measurement. The term "pattern recognition" simply implies that signal characteristics are computed and compared to existing criteria to choose only those signals which are within prescribed limits for acceptable measurement. To perform pattern recognition, a set of conditions must be described which can be used to define the difference between usable and unusable signals.

Characteristically, flow in the ascending aorta during systole is towards the transducer placed in the suprasternal notch. Lack of flow during diastole is also a characteristic. Occurrence of significant prolonged flow in the reverse direction away from the transducer is an indication of abnormal aortic flow or flow in a vessel other than the aorta. These and other parameters such as movement of a ventilator, breathing and noise can be used to determine the acceptability of any given signal based upon knowledge of what is normal or reasonable for flow in the ascending aorta.

Measurement of the aortic diameter can be problematic. It can generally be determined echocardiographically or from M mode measurements; however, this requires the use of relatively expensive equipment. It has been known for some time that aortic diameter typically increases with age. Aortic diameter also tends to increase with body surface area. Therefore, an aortic diameter estimate was developed based upon the height, weight, and age of the subject.

The following detailed description is intended to typify a preferred embodiment of the invention. Those of ordinary skill in the art will readily recognize that alterations and variations to many details of the system may be made as desired.

Functional Description

The Doppler is activated with automatic gain control at a gate depth of seven or eight centimeters depending on the height of the patient. Generally, if a patient is less than 5'6" tall, the search will begin at 7 cm depth. If the patient is 5'6" tall or greater, the search will begin at 8 cm because the 7 cm depth would most likely be too distant from the heart to yield a good reading.

Figure 2:
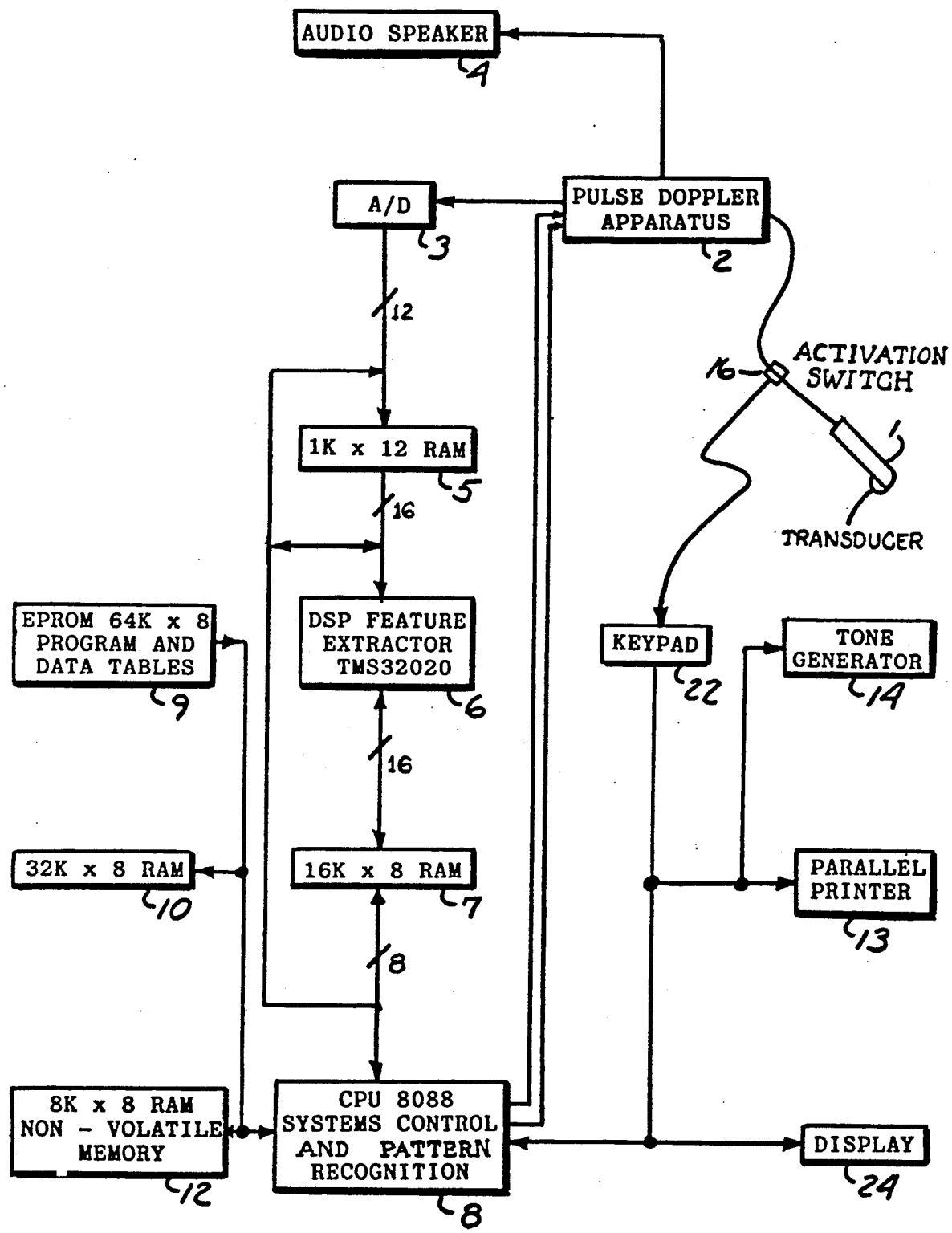
FIG. 2 is a schematic drawing of the device of the invention.

Referring to the schematic drawing of FIG. 2, the Doppler unit (2) transmits a ten-cycle tone burst at 2.4 MHz with PRF of 8.0 kHz and maximum peak-to-peak voltage of 50 Volts to the transducer (1). Within each PRF, a time delay is performed before sampling the Doppler-shifted wave form, resulting in gate depths of 7, 8, 9, or 10 cm. Both the gain of the receiver and the gate depth are controlled by the microprocessor (8).

The Doppler unit detects the in-phase and quadrature signals at the selected gate depth, and these signals are passed to the audio signal output (4) and the 12 bit analog-to digital (a/d) converter (3) The two a/d values are multiplexed to a 1 kByte buffer (5) which forms the time series input to the digital signal processor (6).

At the end of each group of 64 PRF's, or 8.0 ms, the digital signal processor reads a section of the time series data and performs a fast fourier transform (FFT). Features are extracted from the resulting spectrum, stored in a 16 kbyte RAM (7), and passed to the microprocessor (8).

The microprocessor (8) executes instructions loaded from EPROM (9) which stores 64 kbytes of programs and data tables. Information can be selectively stored in a RAM (10) and utilized by the microprocessor. The microprocessor performs pattern recognition upon features extracted by the digital signal processor. In addition, it performs system level control of the device. There are three real-time tasks of the microprocessor: determination of optimal gain, determination of optimal depth of the aortic velocity profile, and maintenance of signal quality during data acquisition at optimal gain and depth.

After twelve systoles are recognized by the microprocessor, the Doppler is turned off and the following values are calculated: cardiac output, cardiac index, stroke volume, stroke index, heart rate, stroke distance, maximum velocity, acceleration, and ejection time.

The full examination results can be optionally sent to the printer (13) and are stored in non-volatile memory (12). A tone generator (14) may be included to signal a user of the device as to predetermined system conditions.

System Hardware

Figure 4:
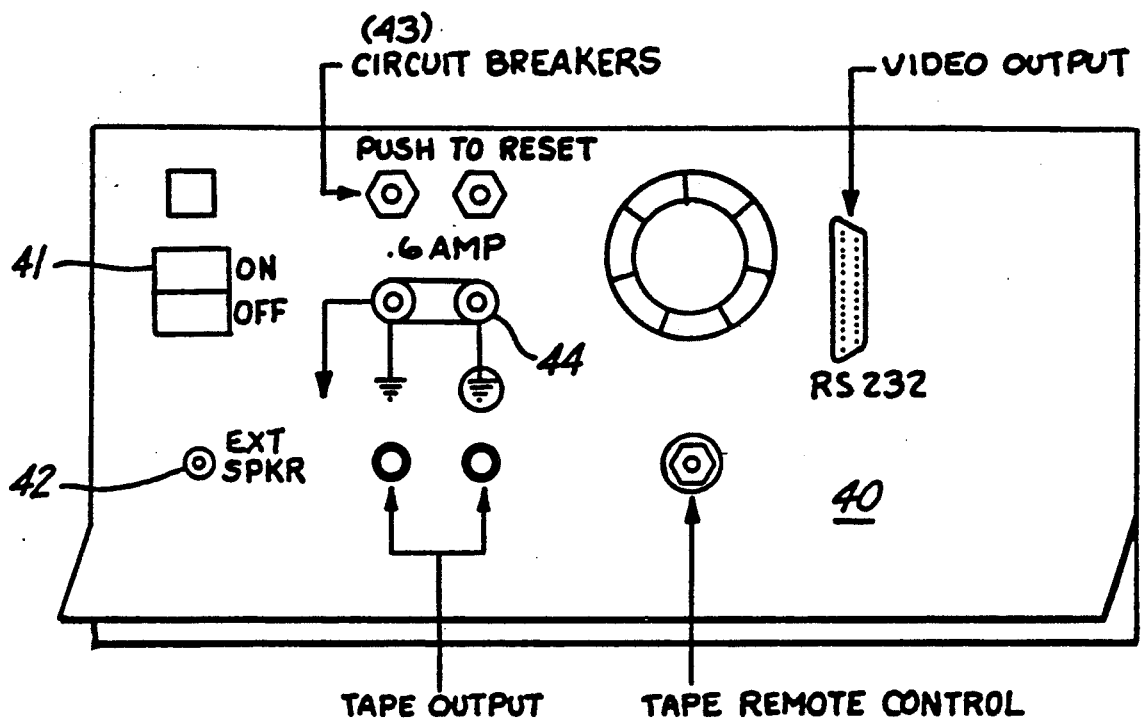
FIG. 4 is an elevation view of the back panel of the device of the invention.
Figure 3:
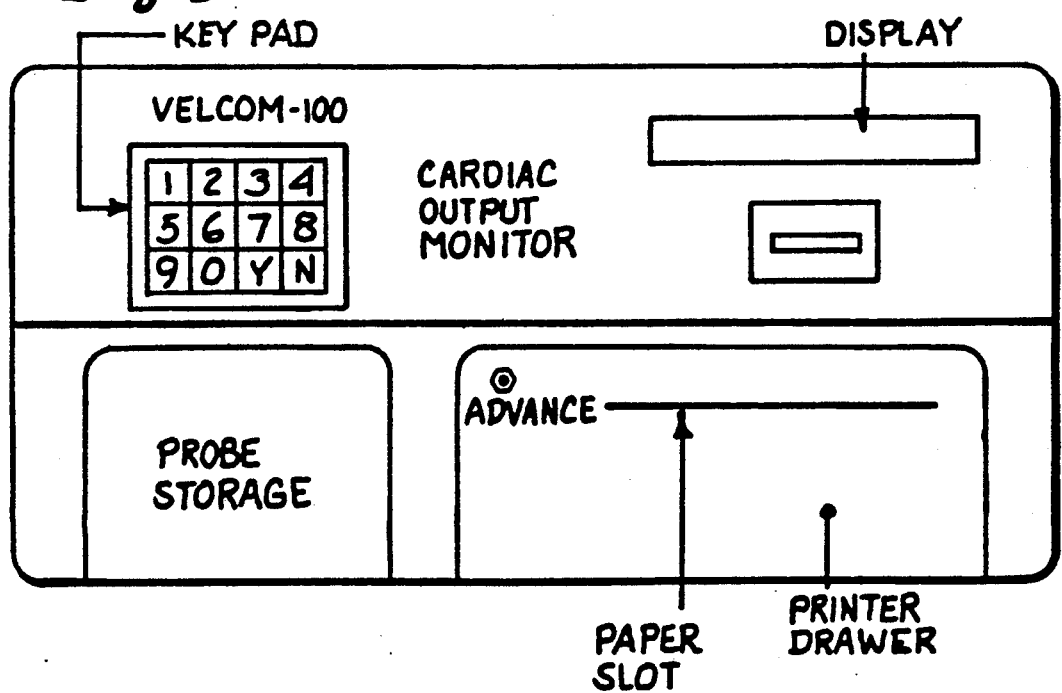
FIG. 3 is an elevation view of the front panel of the device of the invention.

The cardiac output monitor of the invention, in a preferred embodiment shown in FIGS. 1, 3 and 4, comprises a generally rectangular housing (20) having a front panel (21), back panel (40), and a plurality of side panels. The front panel (21) contains the interactive interfaces used by the operator to input information to the device and to receive information and printouts from the device.

An interactive visual display (24) is carried by the front panel (21) to display information pertinent to the examination. The visual display (24) preferably comprises a twenty space LED read-out for displaying information and to guide the operator through a patient examination. The interactive visual display (24) utilizes an alphanumeric single line display to relay complex information obtained in the process of the examination and to display a continuous bargraph corresponding to blood flow detected by the transducer probe (31).

A volume control (25) is carried by the front panel (21) enabling the operator to adjust the volume of an audio signal output to an audio speaker, designated as (4) in FIG. 2, which may be at any desired location on the monitor, the signal corresponding to blood velocity.

A printer drawer (26) may open from the front panel (21) of the cardiac output monitor and preferably contains a printer (shown as (13) in FIG. 2) to print the results of the examination. The printer drawer (26) desirably includes a forwardly facing panel upon which is carried an exit port (32) for the printer paper (28) enabling the operator to receive a hard copy printout of the examination without having to open the printer drawer (26). A paper advance button (27) is conveniently located on the forwardly facing printer drawer panel (26) enabling the operator to advance the paper

(28) so that it may be removed from the device without damaging the readability of the paper.

The front panel (21) of the cardiac output monitor also includes a finger operated keypad (22) through which information is input to the system and the examination is controlled. The key pad (22) comprises at least 12 keys arranged in a grid pattern with ten keys representing the numbers 1,2,3,4,5,6,7,8,9,0, one key representing start/yes, and another key representing stop/no. In order to enter data into the device the operator must press the appropriate keys on the key pad (22) in response to prompts appearing on the visual display (24).

A probe storage drawer (23) is carried by the front panel (21) providing a convenient and protective storage space for the probe (31) when it is not in use. The storage drawer (23) includes a cover which may have a small opening (33) along an edge through which the wire (29) attached to the transducer probe (31) may protrude outwardly of the storage drawer (23) while the drawer is in a closed position. The probe wire (29) may be connected to the device by means of an outlet jack carried by one of the interior walls of the probe storage drawer (23). The probe wire (29) may include an activation switch (30) to control the probe (31).

Carried by the back panel (40) of the device, as shown in FIG. 4, the on/off power switch (41) is used to enable and disable electric power to the device. This switch (41) may comprise a simple on/off toggle switch or the like.

An external speaker output jack (42) is provided on the back panel (40) so that an external speaker may be connected to the device enabling the audio output to be heard at another location. The external speaker may comprise a pair of headphones enabling the operator of the device to hear the audio signal with minimal distraction. Circuit breaker reset buttons (43) are carried by the back panel (40) to enable the operator to reset the circuits if they should become disabled, and one or more external grounding terminals (44) are carried by the back panel (40) to enable the device to be connected to a ground.

The device detects blood flow in the ascending aorta through the use of a pulsed Doppler transducer (31) which is positioned and manipulated within a patient's suprasternal notch. Preferably, the transducer probe (31) is of a commonly used type such as one having a single fixed focus beam emitted from a transducer head. As shown in FIGS. 8 and 9, the transducer probe preferably has a point of focus at a distance (d) of between 7 and 10 cm from the transducer head. The transducer head preferably comprises a single crystal for transmitting and receiving ultrasonic energy signals.

A schematic diagram of the device is shown in FIG. 2. The major system components include a pulsed Doppler apparatus (2), a digital signal processor such as the TMS320C25 (Texas Instruments) (6), and a microprocessor (8) such as the model 8088 (Intel Corp.) or V20 (NEC Corp). The information processing and system control may be done by the 8088 microprocessor or by a similar device. These components are readily available, standard computer parts whose functions will be discussed in detail in the pages to follow.

Operational Modes

The device of the invention utilizes two operational modes during which the Doppler is active. They are (1) "search in depth" mode and (2) "acquisition" mode. During the "search in depth" mode, the device varies the gate depth while taking data. At each gate depth, the user manipulates the probe in the suprasternal notch of a patient in search of a good signal. At the same time, the device performs real time pattern recognition of the received signals until twelve heart cycles have been observed that pass the pattern recognition criteria. During "acquisition" mode, the device holds the depth constant and the user again manipulates the probe in the suprasternal notch of a patient until the device collects twelve heart cycles that pass the pattern recognition criteria.

Figure 5:
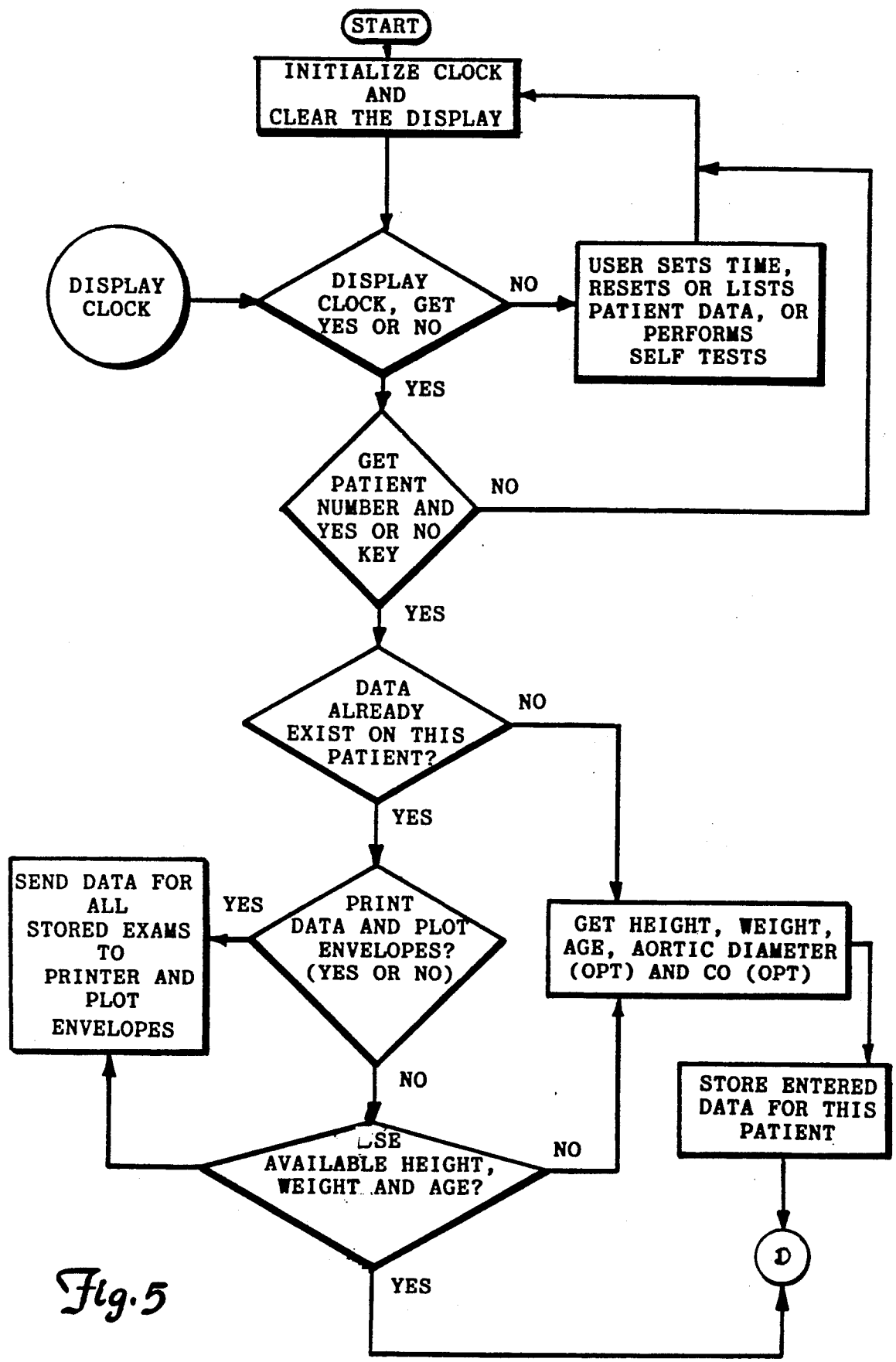
FIG. 5 is a schematic diagram of a data input sequence used in the device of the invention.

FIGS. 5, 6 and 7 diagram the processes of the device in its two operational modes. In these figures, "D" generally refers to "search in depth" mode, and "E" refers to "acquisition" mode.

System Operation

In order to operate the cardiac output monitor typified herein, the device is connected to a power source. The date and time will appear on the visual display indicating that the device is ready for use. The "start/yes" button is pushed to start the examination to which the device responds by displaying "Patient XXXXXXX".

The patient number is then entered using the key pad on the front panel. If an error is made, "stop/no" is pressed to clear the number and then the number may be entered again. When the correct number is displayed, the "start/yes" button is pressed to enter the number into the computer.

If a trial has been completed using the patient number just entered, "Use stored data?" will appear on the screen inquiring if the examination should be taken using data stored previously. If the height, weight, and age of the patient have not changed, "yes" is pressed. Next "Print Data?" will appear. Answering "yes" will cause the device to print the results of previous trials.

If the height, weight or age of the patient have changed, or if the patient number is new, the computer will then ask for height, weight, and age of the patient and these values should be entered using the key pad. The "start/yes" button must be depressed after each number is entered to continue the program. If unreasonable data is entered, (e.g., 5'12"), "Input out of range" will appear. Pressing "start/yes" will remove the message and repeat the previous question. Pressing "stop/no" will abort the current trial and time and date will reappear on the visual display.

Cardiac output can be measured on patients known to have an unusual aortic diameter by the following method. When "aortic diameter? y/n" appears on the display, "yes" is pressed. The display then requests the aortic diameter in centimeters. The measurement is entered to one decimal place. If the aortic diameter is not known, "no" is pressed after this question, causing the device to estimate aortic diameter using the height, weight and age values that were entered at the beginning of the examination.

If the patient has a thermodilution catheter in place, the aortic diameter can be determined by the device using a back calculation. When "cardiac output? y/n" appears on the display, "start/yes" is pressed to invoke the option. The display will request cardiac output in liters per minute. The current thermodilution cardiac output is then entered.

In the preferred system being described, all manually entered input must be within the ranges specified below:

| Patient number | 0 to 9,999,999 |
|---|---|
| Height | |
| (feet) | 4 to 7 |
| (inches) | 0 to 11 |
| Weight (pounds) | 50 to 400 |
| Age (years) | 0 to 120 |
| Aortic diameter (cm) | 1.0 to 5.0 |
| Cardiac output (l/min) | 0.5 to 12.0 |

Entered values are stored in non-volatile memory (12). At this time, the prompts "Place probe . . . " and "Push switch to start" will appear on the display. The patient is placed in a supine position, and a generous amount of ultrasound gel is applied to the probe face. The probe is gripped similar to the way a pencil is gripped for use and it is placed in the patient's suprasternal notch at an angle of approximately 90 degrees with respect to the sternum, with the probe face pointing inferiorly. The probe is pressed firmly enough to allow the probe face to protrude behind the sternum. The examination is started by pressing the probe switch (16). A 7 or an 8 and "Find peak signal" will appear on the display, indicating the depth in cm that the device is looking at for a return signal. "Search in depth" mode has now been activated.

The probe angle with respect to the sternum is slowly maneuvered in the range of 30 to 90 degrees, while the operator observes the display. The best signal is found when the following occurs in conjunction with the display of an "S": the bar graph of velocities extends as far as possible to the right, there is little or no noise visible on the bargraph during diastole and systolic flow sounds emitted from the audio speaker are as high pitched as possible. A poor signal can often be improved by pressing in further with the probe to move the transducer head inwardly of the sternum. When the operator determines that the best signal has been located, the probe is then held still and the probe switch pressed, causing the device to collect 12 heart cycles suitable for calculation of cardiac output.

Before the operator presses the probe switch, a "?" is shown to the right of the depth on the display. After pressing the probe switch, the "?" changes to a ">". The pattern recognition system is now active, and will display an "S" in the far right hand segment of the display for each heart beat for which the AVP passes the acceptance criteria. If the "S" never or rarely appears, the operator must reposition the probe to where the "S" appears as frequently as possible.

The device will search through 7, 8, 9 and 10 cm depths testing for the best depth at which to measure cardiac output. If the device finds no acceptable flow at any depth, this condition is displayed and the "user search mode" is reactivated. Otherwise, the "acquisition" mode is activated at the already determined best depth.

During the first six seconds of "acquisition mode", a ")" is shown to the right of depth on the display. During this time, the automatic pattern recognition of good signals is not active. After six seconds, a ">" replaces the ")", indicating the pattern recognition has become active. The initial six seconds are meant as a time for the operator to re-locate the best signal by manipulating the probe.

If the pattern recognition does not complete a trial within several dozen heart cycles, whether during "search in depth" or "acquisition" mode, the operator may terminate the trial at that depth by depressing the probe switch for a period greater than 0.25 seconds. Doing this maneuver during "search in depth" mode will cause the device to jump to the next depth. During "acquisition" mode, the device will ask the operator whether or not to repeat the "search in depth". If the operator does not choose to repeat the "search in depth", the device aborts the current examination displays the date and time.

Cardiac output and heart rate are displayed after the successful completion of an "acquisition" mode. Pressing the probe switch at this time causes the device to re-execute the "acquisition" mode. Pressing a "yes" at this time allows the operator to print results and end the exam. Pressing "no" aborts the current study and the device displays the date and time.

The power switch on the back panel of the housing should only be turned off when the device is displaying the date and time. If it is desired to turn the system power off when the date and time are not displayed, press "stop/no" and the date and time will appear.

If results are obtained, the device may first display either or both of two warnings before displaying the results. The first warning is "Warning: reverse flow", and indicates that significant flow was detected in the reverse flow direction. The second warning is "Warning: High veloc", and indicates an abnormally high flow velocity detected for this patient. The warnings are meant to suggest the presence of a pathological abnormality or noisy signal for which the calculated cardiac output might be unreliable.

Up to five tests may be stored for each patient number. When a sixth or subsequent test is stored, the oldest test is deleted from memory. A printed report is obtained by pressing "yes" in response to "Test complete-print". This report will contain the previous 1 to 4 stored trials and the current trial. To do another test on the same patient, "yes" is pressed in response to "Repeat test? y/n". The device then returns to "acquisition" mode. If an hour or more elapses before doing a trial again on the same patient, an abbreviated form of the "search in depth" mode is performed at the depths nearest the already chosen optimal depth. At this time, signal characteristics are re-assessed and a new optimal depth is chosen.

Description of Pulse Doppler Receiver

The Doppler receiver can be divided into two RF stages and five audio stages. The RF-preamp and inter channel isolation network (emitter followers) comprise the two RF stages. The five audio sections are: the demodulator with its low pass filter; the sample-and-hold with low frequency canceller; the smoothing filter; the programmable band pass filter; and finally the quadrature balance stage. All stages have gain.

The RF-preamp is a fairly broad band amplifier, from 1.5 Mhz to 5 Mhz. At 2.4 Mhz, the gain of the RF-preamp can vary from 18 to 52 dB in 255 steps. The demodulator circuit has 20 dB of conversion gain. The demodulator low pass filter has a break frequency at 155 khz with a pass band gain of 18 dB.

The sample-and-hold section following the demodulator uses feedback cancellation of signals below 500 Hz which represent artery wall motion. The overall effective passband of this section is 500 to 4,000 Hz.

The smoothing filter on the output of the sample-and-hold circuit has a low pass response. The corner frequency is 10 khz. The corner frequency is adequate for switching transients of the sample-and-hold transitions. The smoothing filter has 18 dB of gain over its pass band.

The programmable filters have an out of band rejection of at least 50 dB. The filter is set for 0 db in the pass band. The signal pass band is set at 550 to 5.0 khz. The corner can be adjusted as needed.

The final stage, before the A/D converter, is a quadrature balance circuit. This stage allows manual trim of the balance between the two quadrature channels and has 14 dB gain from 337 Hz to 9.5 kHz.

Microprocessor Algorithm Components

Four terms are used frequently in referring to the software of the device. The "envelope" is a collection of 125 blood velocity values calculated per second by the digital signal processor. The "first moment" is the sum of a magnitude-frequency product: [i*f(i)], where f(i) is the ith magnitude determined from the 128 point complex FFT (see section entitled "Digital Signal Processor Software Description" below). The "first moment" (FM) is obtained by the formula FM=SUM[i=b 1,N](i*f(i)), where N indicates the number of positive magnitudes of interest. FM is a function that remains close to zero during diastole and rises steeply away from zero during systole. The "first moment derivative" is a value which represents the amount of change per unit time of the averaged first moment values.

The energy of forward flow is calculated by the device using the following formula: EFF=SUM[i=1,N] (f(i)*f(i)), where EFF is the energy of forward flow in units of volts, N is the number of positive magnitudes, and f(i) is the ith spectral coefficient.

Forward flow is determined to be occurring if the first moment exceeds the value T1 and the energy of forward flow exceeds the value T2. T1 and T2 are thresholds that are later defined in equations 1.3 and 1.4, respectively, and are updated at the end of every two second period. If forward flow is determined not to be occurring, then the value of zero is given to the microprocessor as the value of the envelope. Otherwise, a sum is begun from the highest frequency of spectral energy. The spectral energy for the next lowest frequency is added to the sum until the sum exceeds one-fourth of the total spectral energy. The frequency at which this occurs is given to the microprocessor as the value of the envelope.

The envelope, the first moment, the averaged first moment, and the derivative of the averaged first moment are each calculated 125 times per second. These values will be hereafter respectively referred to as IENVEL, FM, CAVER, and DERIV. These values are stored in arrays over time, so the most recent 256 values of each are always available. Thus, when adding an index to these variable names, we are referencing the value that occurred at a particular time, e.g., IENVEL[i] indicates the ith value of the envelope, FM[i−2] indicates the (i−2)th value of the first moment, etc.

The primary components of the microprocessor algorithm determine the following values or events: threshold used in determining the start of systole, the start of systole, whether an AVP is acceptable, the first moment average and its derivative, the real time bargraph, the selection of optimal depth, heart rate, correlation of velocity signals from different heart cycles to produce one representative envelope, calculation of aortic diameter and body surface area, and calculation of the values of cardiac output, cardiac index, stroke index, maximum velocity, peak acceleration, and ejection time.

These algorithm components can be separated into those jobs done in real time, i.e., while the transducer and the digital signal processor are both active, and those jobs not done in real time, i.e., when the transducer is inactive.

A. REAL TIME JOBS

1. Thresholds Calculated in the Microprocessor Software for Use in Determining Systolic Flags There are two thresholds in the microprocessor software that are fundamentally involved in detecting the occurrence of a systole. DMAX is a value the derivative of the averaged first moment must exceed for recognition of a systolic event, and CMIN is a value that must be exceeded for recognition of a systolic event. It is necessary to have information in these thresholds that spans more than two seconds if a minimal number of false systoles are to be detected. False systoles can come from noise spikes during a time of little signal, such as when breath motion or searching with the probe takes the field of view away from the aortic signal.

The methods for finding CMIN and DMAX are essentially the same. First, the running maximum of the first moment, FMmax, and running maximum first moment derivative, DERIVmax, are calculated by keeping track of the maximums of FM and DERIV across 256 iterations, roughly two seconds. Also denote CMIN' and DMAX as the most recent values of CMIN and DMAX. The next values of CMIN and DMAX are calculated by the following equations:

$$DMAX = \begin{bmatrix} \text{If DMAX'/DERIVmax} > 0.6, \\ 0.4 * \text{DERIVmax} \\ \text{If DMAX'/DERIVmax} < = 0.6, \\ (0.8 * \text{DERIVmax} + \text{DMAX'})/3. \end{bmatrix}$$

$$CMIN = \begin{bmatrix} \text{If CMIN'/FMmax} > 0.15, \\ 0.1 * \text{FMmax} \\ \text{If CMIN'/FMmax} < = 0.15, \\ (0.2 * \text{FMmax} + \text{CMIN'})/3. \end{bmatrix}$$

The effect of this method is that wall thumps and other large energy non-systolic signals (temporarily seen) by the device will not cause the thresholds for detecting systoles to become suddenly too high.

2. Calculation of First Moment Average and Its Derivative

The first moment average, CAVER, is calculated before taking the first moment derivative, DERIV. CAVER is a six point moving average of FM starting with the current iteration and including the five next previous iterations. The derivative is then calculated by the rule: DERIV[i]=(CAVER[i]+CAVER[i−2]−CAVER[i−12]−CAVER[i−14])/2. Here the derivative need not be normalized.

3. Determination of a Sysolic Chart

The following are six criteria that must be met for a systolic start to be recognized by the device (note this is different than the task of discriminating whether an occurred systole can be used for calculation of cardiac output):

a) The first moment, FM, has reached a minimum steepness, DMAX.

b) 240 ms ago, the envelope IENVEL depicts an absence of flow.

c) The current envelope depicts flow.

d) The derivative of the first moment average, DERIV, has reached a local maximum.

e) The previous systole occurred more than 400 ms ago.

f) The first moment, FM, has exceeded a minimum value, CMIN.

4. Barograph Algorithm

Preferably, the bargraph displays a visual representation of a signal corresponding to blood flow velocity from 0.0 to 4.5 kHz on any of a variety of 20 character alpha numeric displays whose characters are made up from 5 by 7 dot matrix elements. Any signal above 4.5 kHz is displayed as 4.5 kHz.

In a preferred embodiment, the display contains a total of twenty characters, sixteen of which are used for the bargraph, two for display of depth (leftmost two characters) one for a bargraph active indicator (">", ")", or "?" to the right of depth), and one for a "good" systole indicator (an "S" at the far right box). The instantaneous modal frequency is displayed by a row of solidly lit 5×7 characters corresponding to increasing frequency as characters are lit from left to right. Referring to the bargraph active indicators, a "?" indicates the device is searching in depth for the best signal, a ")" indicates data is not presently being acquired, and a ">" indicates data is presently being acquired. Signals above 4.5 kHz, corresponding to high blood velocities, are clipped to the upper end of the bargraph (e.g., box #18 of 0–19) so that signals corresponding to velocities below 1.5 m/s are given the greatest attention.

The device additionally displays persistently a row of colons residing in the "background" of the solid characters. This row of colons represents the average peak systolic velocity for the preceding four systoles. The peak velocity for a given systole is determined by finding the maximum "envelcpe" value during a 100 ms time span, whose center is the systolic indicator. If no systole occurs for approximately three seconds, then the row of colons is cleared and the four beat average is restarted.

Figure 10A:
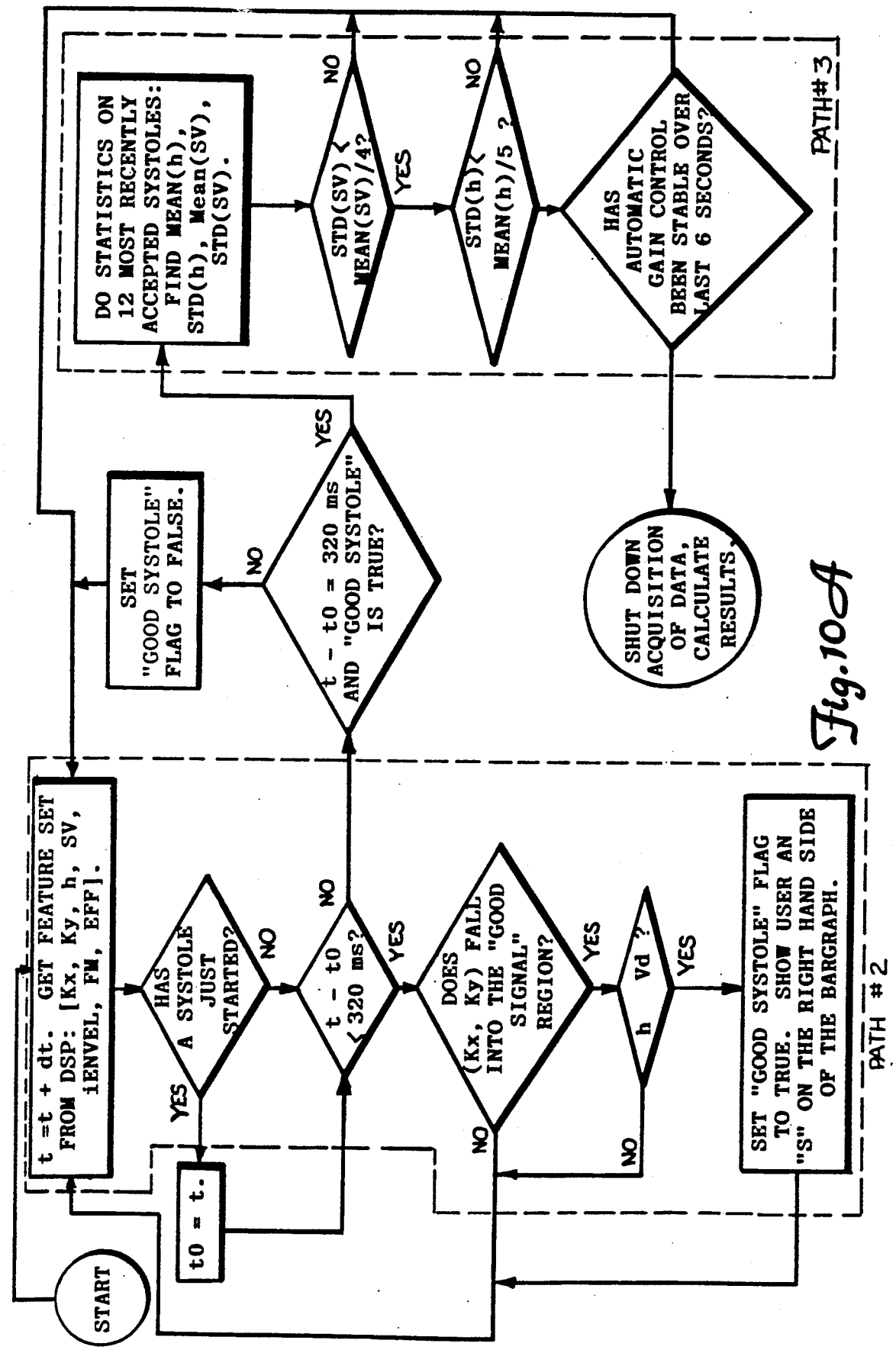
FIG. 10A is a schematic diagram of another portion of the real time pattern recognition mode utilized in the device of the invention.

5. Pattern Recognition of Signals Suitable for Calculation of Cardiac Output There are three parallel paths comprising the pattern recognition algorithm of the preferred embodiment. Path #1, which exists in the digital signal processor, is shown in FIG. 10 and described in the section entitled DIGITAL SIGNAL PROCESSOR SOFTWARE DESCRIPTION. Paths #2 and #3 exist in the microprocessor and are shown in FIG. 10A.

Path #2 is used to determine if the velocity profile following the most recent systolic flag should be included in the calculation of cardiac output. This decision must be made during the 320 ms following the detection of a systolic event (see section #3) The decision is affirmative if two conditions are simultaneously true at some point during the 320 ms window. The first condition is that the normalized Karhunen Loeve parameters K1 and K2, calculated in the DSP, obey the following rule:

$$\left\{ \begin{array}{l} K2 < 0.417 * K1 + 24.2 \text{ if } K1 < -16.1 \\ K2 < 0.497 * K1 + 28.0 \text{ if } K1 >= -16.1 \end{array} \right\} \quad \text{Eq. 5.1}$$

The second condition is that the maximum value over the past 400 ms of the median filtered velocity profile, h, is greater than Vd. Vd, the "desired velocity" to be observed, is a value derived during search mode. The calculation of Vd is described in the section entitled "DETERMINATION OF THE DEPTH CONTAINING THE OPTIMAL SIGNAL." Generally when an operator moves away from the signal in the center of flow, the maximum velocity, h, will decrease. The second condition thus acts to keep the probe trained on the best possible signal.

If the observed velocity profile satisfies the conditions of path #2, then the systole is loaded into the top of a "systole buffer," and all other systoles are displaced one step backward in the same buffer. If twelve systoles exist in the systole buffer, then path #3 determines (1) if the standard deviations of maximum velocity and stroke distance across the buffer are respectively within 20% and 25% of their means, and (2) if the automatic gain control has not been steadily rising or falling during the past six seconds. The effect of path #3 is to not allow the exam to be completed unless the group of twelve observed signals can be said to contain a certain resemblance to each other. If the path #3 conditions are true, then the exam is concluded and the cardiac output and related parameters are determined.

(a) DERIVATION OF EQUATION 5.1

Equation 5.1 was found through statistical analysis of two independent groups of aortic velocity profiles. The first group of AVPs was used to determine an efficient way to represent the signal class of all AVPs, by use of the discrete Karhunen Loeve (KL) expansion. The derived KL expansion was applied to the second group of AVPs. On the second group of AVPs, a pattern recognition boundary based on two KL coefficients was found that separated signals suitable for calculation of cardiac output from signals not suitable for calculation of cardiac output. This pattern recognition boundary (Equation 5.1) was chosen to yield a 16% false alarm probability, and results in a detection probability of 0.84.

(i) THE FIRST GROUP OF AVPs: Applying the Karhunen-Loeve Expansion

The first group of AVPs was assembled from the averaged results of each of 234 studies on both normals and intensive care patients. From this set of average AVPs, 164 were selected which fell well within the range of signals characteristic to the ascending aorta.

Figure 11:
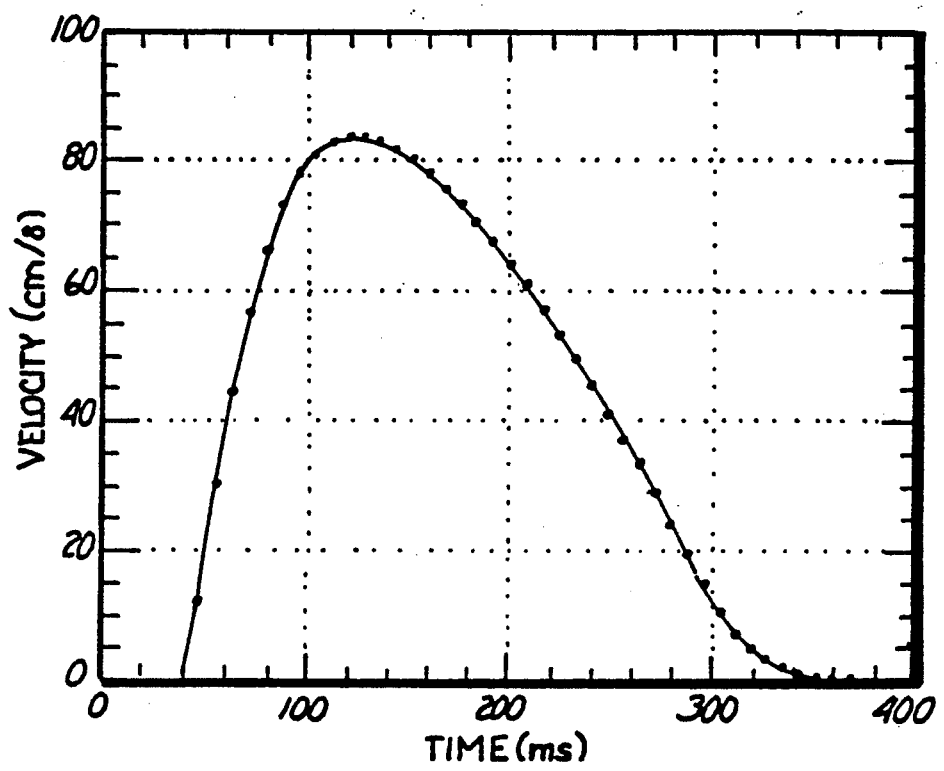
FIG. 11 is a graph showing an average aortic velocity profile.

The set of 164 averaged AVPs forms the signal class $[X(i): i=1,164]$. Each AVP contains 50 discrete values and a sample period of 8.0 ms, yielding a total length of 400 ms. The average of all signals in $[X]$ is shown in FIG. 11, and is denoted by M. The discrete Karhunen-Loeve expansion was applied to $[X]$ to determine a small set of K orthogonal eigenvectors, $[p(i): i=1 \ldots K]$, defining the space containing the predominant signal class energy.

$[p]$ was derived by first constructing the zero mean set $[X': X'(i)=X(i)-M, i=1 \ldots 164]$. The covariance or average outer product matrix was formed by the rule $$G(j,k) = E[X'(i,j), X'(i,k)], \ j,k = [1,50],$$

where X'(i,j) is the jth value of the ith signal X'(i).

G was decomposed into fifty eigenvectors [P(i): i=1,50] and eigenvalues [L(i): i=1,50], where P(i) and L(i) are ordered from greatest eigenvalue (L(1)) to least eigenvalue (L(50)). L(i) is proportional to the energy of the signal class (X') in the direction of the corresponding ith eigenvector.

The set [p] consists of the first K vectors of the set [P]. In particular, for any fraction of the total signal class energy, there is a minimum value of K such that the predominant energy of the signal class [X'] is still contained in [p]. The relative values of the four (K=4) largest eigenvalues of [L] are shown in FIG. 12, and the corresponding eigenvectors p(1) . . . p(4) are shown in FIG. 13. These four eigenvectors together span a space containing 90% of the signal class energy. Any AVP, A, can be efficiently represented by the values K1, K2, K3, and K4:

K1 = <A−M, p(1)>
K2 = <A−M, p(2)>
K3 = <A−M, p(3)>
and K3 = <A−M, p(3)>.

NOTE: The notation <a,b> denotes the dot product between the vectors a and b.

(ii) THE SECOND GROUP OF AVPs: Deriving a Pattern Boundary

The second group of AVPs, [Y], was assembled from over 3300 non-averaged aortic velocity profiles sampled from both normals and intensive care patients. [Y] was divided by experts into signals suitable for calculation of cardiac output, [YG], and signals not suitable for calculation of cardiac output, [YB]. AVPs in [YB] are typically corrupted by noise, or contain an abnormally short systolic interval. [YG] contains 2445 AVPs, and [YB] contains 867 AVPs.

Experiments showed that K1 and K2 are clearly important in separation of [YG] from [YB], but only after pre multiplying each signal Y(i) by the factor Nu, where Nu=max(M)/max(Y(i)). K1 and K2 were determined for each signal Y(i) after multiplying by Nu. A modified simplex search algorithm was then used to find the linear pattern boundary, K2=f(K1), which optimizes the detection of [YG] without allowing more than 16% false alarms from [YB]. The optimized detection probability of [YG] is 0.84, and the resulting pattern boundary is Equation 5.1.

Reference for modified simplex search algorithm: [Reklaitis, et al., *Engineering Optimization*. Wiley and Sons, New York: 1983, pp. 76 ff.]

(b) NOTE ON THE REAL TIME IMPLEMENTATION OF EQUATION 5.1

Equation 5.1 was constructed from the AVP groups [X] and [Y]. The left edge of every AVP in [X] and [Y] was aligned at 40 ms before any analysis was performed. In real time, the window containing the "current signal" is moving in time, and rarely is the left edge of systole located at 40 ms into this window. Equation 5.1 is still valid without any alignment of the real time AVP if two conditions are observed. The first condition is that given the AVP A, the factor Nu is modified in the following way:

$$Nu = \begin{bmatrix} 0 \text{ if EITHER max}(A) = 0 \\ \text{OR any of the first 5 values} \\ \text{of A is not 0.} \\ \text{max}(M)/\text{max}(A) \text{ OTHERWISE} \end{bmatrix}$$

This condition is implemented in the digital signal processor (see DITIGAL SIGNAL PROCESSOR SOFTWARE DESCRIPTION and FIG. 10). The second condition is that Equation 5.1 can only be applied to accept or reject an AVP during the 320 ms following a systolic start. This condition is implemented in the microprocessor.

B. JOBS NOT DONE IN REAL TIME

1. Determination of the Depth Containing the Optimal Signal

Twelve systoles are sampled at each depth during the "search in depth" mode. This set of aortic velocity profiles is denoted by B=(b1,b2, . . . , b12). The maximum average velocity for a given depth, Vmax, is calculated as follows:

(a) Median filter and zero the diastolic section on each of the profiles of B as described later in parts (a) and (b) of the CORRELATION AND DATA REJECTION ALGORITHM below.

(b) For each profile, bi, find the maximum value of a "reconstructed" profile, Vi, according to the following formula:

$$Vi = \text{maximum} \\ [M + K1^*E1 + K2^*E2 + K3^*E3 + K4^*E4]$$

where M is the mean aortic velocity profile E1 . . . E4 are the Karhunen-Loeve eigenvectors with the four largest eigenvalues K1 = <bi−M,E1>
K2 = <bi−M,E2>
K3 = <bi−M,E3>
K4 = <bi−M,E4>

NOTE: The notation <a,b> denotes the dot product between the vectors a and b.

(c) Now with the set of reconstructed maxima, (v1,v2, . . . ,v12), find the average value:
Vmax=mean(v1,v2, . . . ,v12).

The optimal depth is typically the depth whose Vmax is largest, unless Vmax for seven cm is the largest and Vmax for eight cm is the least. In that case, it is assumed that the innominate artery is actually at seven cm and the aorta is deeper. Under this condition, nine or ten cm is chosen as the depth of interest, whichever produced the highest value of Vmax.

Now the "desired velocity" for this optimal depth, Vd, is calculated as 85% of Vmax. For future measurements of cardiac output, the operator will be required to locate signals whose maxima, after median filtering and zeroing the diastolic sections, exceed Vd.

2. Determination of Heart Rate

Heart rate is calculated from the modal average systolic flags. Since twelve heartbeats are collected during the data acquisition mode, there are eleven resulting values of "time between systolic flags". Call these values D=[d1,d2, . . . ,d11]. A value dm is defined as the value in the D which has the greatest number of remaining values in D falling within +/−20% of its own magnitude. If the number of values falling within this +/−20% range of dm does not exceed five, then the examination is rejected due to a lack of confidence in the heart rate calculation. If the number of values falling in the +/−20% range of dm exceeds five, then the mean average of this group, including dm, is reported as the time between systoles. The reciprocal of this reported value is the heart rate in beats per minute.

3. Correlation and Data Rejection Algorithm

When a "good" systole occurs (see section #5 of JOBS DONE IN REAL TIME), the envelope IENVEL across the duration of that systole is stored in memory. The stored IENVEL values for one systole have been previously defined as an AVP. There are four steps involved in taking these stored systolic profiles for twelve heartbeats and producing one representative systolic profile:

a) Median filter all stored AVPs to remove non-physiological variations in apparent AVPs. Define b1 to be a stored AVP. When this stage of the algorithm is reached, there exists a set of twelve AVPs: (b1,b2, ... ,b12). b1[i] is the ith in time value of b1. The median filter applied to each value of the stored AVP b1 is defined as:

$$a = (b1(i-2) + b1(i-1) + b1(i+1) + b1(i+2))/4$$

if abs(a−b1(i))>21 cm/s then b1(i)=a
This filter is performed so that the unfiltered values b1(i) and b1(i−1) are used in filtering b1(i+1).

b) Zero the diastolic portion of each stored AVP. On each AVP first locate the time of the ascending portion that is 32 ms or 4 iterations before the 20% of maximum velocity point. Call this kstart. Similarly, locate the time of the descending portion that is 32 ms or 4 iterations after the 25% of maximum velocity point. Call this kstop. Then zero all values before kstart and after kstop.

c) Correlate and average the twelve stored systoles. If x, y and z denote stored systolic profiles, then let the cross-correlation function x=C(y,z) denote the operation of aligning y and z via a maximum in the cross correlation function and storing the resulting average systolic profile to x. The following recursive sequence of operations is performed:

x=C(b1,b2)
x=C(x,b3)
x=C(x,b4)
x=C(x,b5)
x=C(x,b6)
x=C(x,b7)
x=C(x,b8)
x=C(x,b9)
x=C(x,b10)
x=C(x,b11)
x=C(x,b12)

d) Sum the elements stored in x and divide by 12 to yield the average correlated systolic velocity profile.

4. Determination of Aortic Diameter and Body Surface Area

A paper titled, "Nomogram for Determining Normal Aortic Diameter (Aortic Arch) and Aortic Biological Age in 2-m Chest X-Rays" by Strehler, et al., CIBA-GEIGY Limited, CH-4055 Basle, Switzerland was used as a reference for determining a formula for body surface area. An analysis of this paper was performed regarding calculation of aortic diameter in comparison with m-mode root aortic measurements done at Providence Medical Center, and a linear correction to the CIBA-GEIGY results was added.

The formula used to calculate body surface area is:

$$BSA = \exp(\log(L) + \log(G)/3.0 \; \log(3.85))/100.0.$$

In this formula, G is weight (in kilograms), and L is height (in cm). Aortic diameter is found using the following formula:

$$adiam = 0.98 * gamma + 0.316$$

where $$gamma = \exp(\exp(alpha)) * 1.12 - 0.3$$

$alpha = \log(BSA)/2.0 + \log(\log(A)) - \log(5.15)$. A is age (in years)

5. FORMULAS FOR FINAL VALUES $$CO = SV*HR/1000. \text{ (liters/min)}$$

where
HR=Heart rate, algorithm described separately.
SV=SD*3.1415926*adiam*adiam/4 (cc)
SD=Stroke distance m/s (Trapezoidal integration of the flow velocity profile over the systolic period from t0 to t1) cm/s.
t0=Leading edge of systole determined by going backward in time from the peak to the 2nd profile element below 20% of the peak or the first 0 point below 20% of the peak, whichever occurs first. Each profile element is spaced by 8.005 mx in time.
t1=Lagging edge of systole determined by going forward in time from the peak to the 2nd profile element below 25% of the peak.
adiam=aortic diameter, cm.
CI=Cardiac Index (liters/min/sq meter)=CO/BSA
where
BSA=Body surface area, sq meters.
Stroke Index=SV/BSA. (cc/sq meter)
Maximum Velocity=Maximum value of flow velocity profile, cm/s.
Accleration=Peak instantaneous acceleration value, meters/sq second, as calculated with the following algorithm and 16 point finite impulse response (FIR) filter:

ALGORITHM FOR CALCULATION OF ACCELERATION (a) Find i such that velocity [i+1]−velocity[i] is maximum for whole profile.
(b) At j=i and j=i+1 perform the 3 point average velocity [j]=(velocity[j+1]+velocity[j]+velocity[j−1])/3
(c) Apply derivative filter to velocity[].

filter[0] = 0.15293175E − 2    filter[15] = −filter[0]

filter[1] = −0.24424011E − 2   filter[14] = −filter[1]

filter[2] = 0.20143061E − 2    filter[13] = −filter[2]

filter[3] = −0.26991114E − 2   filter[12] = −filter[3]

filter[4] = 0.42867465E − 2    filter[11] = −filter[4]

filter[5] = −0.82355430E − 2   filter[10] = −filter[5]

-continued
filter[6] = 0.22635138E − 1   filter[9] = −filter[6]

filter[7] = −0.20275757E + 0   filter[8] = −filter[7]

(d) Find maximum in resulting derivative.

Ejection Time = $t1 - - t0$ (ms)

Digital Signal Processor Hardware Description

The digital signal processing section of the device comprises a signal processor, an A/D buffer memory, and a program and data transfer memory. The A/D buffer memory is 1024 words long, each word being 12 bits wide. This buffer is a switched type double buffer such that the A/D and the digital signal processor both share the address and data lines. The program memory and data transfer memory is 2048 words long, each word being 16 bits wide. The digital signal processor code operates from this memory. It is preloaded with the program by the microprocessor. This buffer is a switched type double buffer such that the digital signal processor and the microprocessor both share the address and data lines.

Digital Signal Processor Software Description

The digital signal processor code allows 125 sets of features to be calculated per second. The Doppler shift signals are input from the A/D converters, a spectra is calculated, features are extracted from the spectral coefficients and the results are output to the microprocessor.

The input to the digital signal processor is from a circular buffer implemented in hardware. This buffer is 1024 12-bit words long. It is filled with quadrature data from the A/D converter, alternating in-phase and out-of-phase values. The 256 words are read from this buffer into the digital signal processor 125 times per second. These 256 words represent 128 complex pairs. Each set of 256 words overlaps. Error checking occurs to insure that the digital signal processor is synchronized with the A/D state machine.

Once these 256 words are input to the digital signal processor, they are multiplied by a Hamming Window. This window is used to reduce the effects of boundary condition violations. Next, a 128-point complex FFT is performed on the data. The magnitudes are then calculated from the spectral coefficients using a Taylor series expansion. The expansion performs the calculation in either Equation 1.1 or 1.2 based on which of the two coefficients, the real or imaginary, are greater. Since the digital signal processor is an integer processor, a portion of the integer is dedicated to fractional positions.

```
if imaginary > real, then                    Equation 1.1
mag = [(real/2) * (real/imaginary)] + imaginary
if real > = imaginary, then                  Equation 1.2
mag = [(imaginary/2) * (imaginary/real)] + real
```

The resultant 128 magnitudes are then thresholded such that any magnitude falling below a threshold is set to zero. The threshold is set as a constant at the start of the program. In addition, the maximum magnitude is determined.

The next steps involve calculation of the features. The features include the positive flow energy, negative flow energy, first moment, envelope value, Karhunen-Loeve parameters, envelope maximum velocity after median filtering (see section #3 for median filter rule), and envelope integral after median filtering (stroke distance). The positive flow energy is obtained by summing the squares of the magnitudes for coefficients from 1 to N where N is the number of positive flow coefficients. The negative flow energy is obtained by summing the squares of the magnitudes for the coefficients from N+1 to 128.

A set of running globals are also calculated each iteration. These include the running spectral first moment maximum and minimum, and the running energy maximum and minimum. The running maxima and minima are the maxima and minima relative to the current set of 256 iterations. Every 256 iterations, the values "global first moment threshold" and "global energy threshold" are calculated based on the running maxima and minima of spectral first moment and energy.

From the set of 128 magnitudes from one FFT, the first moment (FM) is calculated by summing the result of multiplying each magnitude by the bin number of that magnitude. The envelope (iENVEL) is determined by comparing the integral of the total energy counting top down through the positive magnitude coefficients until the first bin that has an accumulated energy greater than the energy threshold. The energy threshold is equal to the total energy divided by four. The envelope is set to zero if FM is less than the global first moment threshold or if the positive energy is less than the global energy threshold.

The running first moment maximum and minimum and the running energy maximum and minimum are calculated by keeping track of the maxima and minima of these values across 256 iterations, roughly two seconds. The running first moment maximum(minimum) is updated if the local first moment is greater(less) than the running first moment maximum(minimum). The running maximum energy is calculated by adding an energy increment if the total energy is greater than the running maximum energy. This energy increment restricts the rate at which the running maximum energy can rise. The running minimum energy is set to the local total energy if the local total energy is less than the running minimum energy.

The global first moment threshold and the global energy threshold are determined by Equations 1.3 and 1.4, respectively:

Equation 1.3:
global first moment threshold (T1) =
(minimum running first moment) +
((maximum running first moment −
minimum running first moment)/20).

The global first moment threshold is not allowed to fall below a value of 10.

Equation 1.4:
global energy threshold (T2) =
(minimum running energy) +
((maximum running energy −
minimum running energy)/20).

The global energy threshold is not allowed to fall below a value of 10, nor is it allowed to rise above a value of 500.

FIG. 10 shows the DSP path for calculation of the Normalized Karhunen-Loeve parameters Kx and Ky, as well as the stroke volume SV and the maximum velocity h. This flow, noted as Path #1 in this document, is executed every 8 ms. Thus for every calculation of an FFT and a resulting IENVEL value, there is an accompanying calculation of [Kx,Ky,SV,h].

Let S denote the velocity profile spanning the most recent 400 ms. Let S1 denote the resulting profile after median filtering S and zeroing its diastolic sections (see parts (a) and (b) of the CORRELATION AND DATA REJECTION ALGORITHM). Then h is simply the maximum value of S1, SV is the sum of all 50 values contained in S1, and Kx and Ky are found as follows:

$$Kx = <D*S1 - M, E1> \text{ and } Ky = <D*S1 - M, E2>,$$

where $$D = \begin{bmatrix} 0 \text{ IF } (\max(S1) = 0 \text{ OR any} \\ \text{ of 5 oldest values} \\ \text{ of S1 are not 0)} \\ 42.3537/\max(S1) \text{ otherwise.} \end{bmatrix}$$

M is the mean aortic velocity profile
E1 and E2 are the two Karhunen-Loeve eigenvectors with respectively the largest and second largest eigenvalues.
$<a, b>$ is the dot product between the vectors a and b.

Once the features are calculated, the microprocessor is signalled, indicating that the digital signal processor is done with another cycle. The microprocessor then puts the digital signal processor in a hold state, reads the features from the program memory, and releases the digital signal processor.

While a preferred embodiment of the present invention has been described, it should be understood that various changes, adaptations and modifications may be made therein without departing from the spirit of the invention and the scope of the appended claims.

What is claimed is:

1. A cardiac output measuring device for detecting blood flow in a patient's ascending aorta, comprising,
    an ultrasonic transducer probe adapted to be received in the patient's suprasternal notch, including means for generating ultrasonic energy pulses directable toward the ascending aorta when the probe is positioned in the suprasternal notch, and receiving reflected frequency shifted energy pulses having a frequency shift related to the velocity of blood flow through the ascending aorta of a patient,
    electronic means for separating the reflected frequency shifted signals from non-frequency shifted signals to form Doppler shift signals, and demodulating the Doppler shift signals into the normal audio frequency range,
    computing means responsive to said Doppler-shift signals for computing the cardiac output of the patient,
    means for selecting the depth within the aorta of the patient at which the velocity of blood flow is measured, said means comprising means for varying the time interval between the time at which a signal is transmitted and the time the reflected signal received by the ultrasonic transducer probe is selected for processing, the time intervals corresponding to varying distances from the probe and therefore also to linear positions within the ascending aorta,
    pattern recognition means for testing a time series of received Doppler shift signals against predetermined signal quality characteristics and for accepting such signals as meet such characteristics, and
    means responsive to said accepted signals for choosing the linear position within the ascending aorta corresponding to the greatest frequency shift.

2. The cardiac output measuring device of claim 1 including data entry means for entering height, weight and age data for the patient,
    means for estimating aortic diameter from such height, weight and age data,
    means for calculating heart rate using said accepted signals, and
    said computing means responsive to said estimated aortic diameter and the accepted signals for computing cardiac output.

3. The cardiac output measuring device of claim 2 wherein the manual data entry means comprises an electronic keypad.

4. The cardiac output measuring device of claim 1 including manual data entry means for detecting aortic diameter data obtained from external measurements, and means responsive to the aortic diameter obtained from external measurements and the accepted frequency shifted signals for computing cardiac output.

5. The cardiac output measuring device of claim 1 wherein the means for generating and receiving ultrasonic energy pulses comprises at least one piezoelectric crystal.

6. The cardiac output measuring device of claim 1 including means for generating an audio signal having a frequency corresponding to the blood flow velocity calculated in the ascending aorta.

7. The cardiac output measuring device of claim 1 wherein the pattern recognition means for testing a time series of received Doppler-shift signals includes means for calculating Karhunen-Loeve expansion coefficients in real time and means for forming a primary feature set of signal characteristics using the Karhunen-Loeve expansion coefficients.

8. The cardiac output measuring device of claim 1 wherein the pattern recognition means for testing the time series of received Doppler-shift signals comprises:
    means for calculating in real time a set of normalized Karhunen-Loeve expansion coefficients of the time series of received Doppler-shift signals;
    means for calculating in real time a stroke distance and a peak velocity of the time series of received Doppler-shift signals;
    means in real time for determining from the normalized Karhunen-Loeve expansion coefficients whether the time series of received Doppler-shift signals is suitable for calculation of cardiac output;
    means for collecting a plurality of the suitable time series from which to calculate cardiac output;
    means for computing in real time a standard deviation and means of the suitable stroke distances, and a ratio of the standard deviation to the mean;
    means for computing in real time a standard deviation and mean of the suitable peak velocities, and a ratio of the standard deviation to the mean; and
    means in real time for determining from the ratio of the standard deviation of the suitable peak velocities to the mean of the suitable peak velocities and from the ratio of the standard deviation of the suitable stroke distances to a mean of the suitable stroke distances, whether or not to conclude the collecting of the suitable time series, and whether or not to report the cardiac output measurement.

9. A cardiac output measuring device for detecting blood flow in a patient's ascending aorta, comprising
  (a) an ultrasonic transducer probe having a head adapted for insertion in a patient's suprasternal notch,
  (b) means for generating ultrasonic energy pulses and receiving a time series of reflected frequency shifted energy pulses having a frequency shift proportional to the velocity of blood flowing through the ascending aorta,
  (c) means for receiving, and amplifying the reflected frequency shifted pulses,
  (d) means for determining from the magnitude and the direction of the shift frequency, the corresponding velocity of blood flow,
  (e) pattern recognition means for selection of reflected, Doppler frequency shift signals for use in calculating cardiac output, said pattern recognition means comprising means for selecting and accumulating such Doppler shift signals as qualify under all of the following criteria;
  the first moment of and time derivative of such Doppler shift signals indicates blood flow toward the transducer probe in the forward direction, and for a specified period of time preceding the reception of such Doppler shift signals, signals corresponding to blood flow in the direction toward the transducer probe were not detected;
  (f) means for testing accumulated time series of Doppler shift signals against predetermined signal quality characteristics and for accepting and averaging such signals as meet such characteristics,
  (g) calculating means for calculating heart rate from said accumulated time series of signals,
  (h) means for estimating aortic diameter from height, weight and age data,
  (i) computing means responsive to said averaged signal, said heart rate and aortic diameter for computing the cardiac output of the patient, and
  (j) validity testing means responsive to said heart rate and said averaged signal for determining the validity of the cardiac output measurement.

10. A cardiac output measuring device for detecting blood flow in a patient's ascending aorta comprising
  (a) an ultrasonic transducer probe receivable in a patient's suprasternal notch, the probe having means for generating ultrasonic energy pulses directable toward blood flowing in the ascending aorta and receiving reflected frequency shifted energy pulses representative of the velocity of blood flow through the ascending aorta of a patient, said transducer having a handle adapted to be manually held by an operator, and
  (b) visual display means responsive to said received frequency shifted energy pulses for displaying a visual signal representing the velocity of blood flow in the ascending aorta, the visual display signal corresponding to blood velocity of each heartbeat being overlaid upon the signal for the preceding heartbeat on the visual display means, and
  (c) peak indicator means responsive to each of said blood velocity signals for producing a visual flag on said visual display means representing the peak value of each such signal, the peak flag for each signal remaining on the visual display means at least until the next heartbeat peak so that it may be compared with the peak flag position for the next succeeding signal.

11. A method for deriving an efficient set of features with which to perform real time statistical pattern recognition on time series of received Doppler-shift signals, comprising the steps of:
  (a) collecting a large group of time series Doppler-shift signals;
  (b) determining a set of Karhunen-Loeve expansion eigenvectors from the large number of time series of received Doppler-shift signals;
  (c) collecting a second large group of time series Doppler-shift signals and separating said second group into preferred signals and unpreferred signals;
  (d) calculating Karhunen-Loeve coefficients using the Karhunen-Loeve expansion eigenvectors;
  (e) normalizing the Karhunen-Loeve coefficients;
  (f) determining which karhunen-Loeve coefficients are statistically relevant for use in separating said preferred signals from said unpreferred signals; and
  (g) determining a discriminant relation of said statistically relevant Karhunen-Loeve coefficients for use in separating said preferred signals from said unpreferred signals.

* * * * *